United States Patent

Brungs et al.

[11] Patent Number: 5,744,021
[45] Date of Patent: Apr. 28, 1998

[54] 2-ALKYLMERCAPTO-4-(TRIFLUOROMETHYL)BENZOIC ESTERS AND A PROCESS FOR THEIR PREPARATION

[75] Inventors: Peter Brungs, Frankfurt; Thomas Karcher, Altötting; Klaus Kühlein, Kelkheim; Hans Millauer, Eschborn; Manfred Wildt, Brombachtal, all of Germany

[73] Assignee: Hoechst AG, Frankfurt, Germany

[21] Appl. No.: 770,325

[22] Filed: Dec. 20, 1996

[30] Foreign Application Priority Data

Dec. 22, 1995 [DE] Germany ............... 195 48 428.2

[51] Int. Cl.$^6$ ............... C25B 3/00; C07C 321/00; C07C 69/76
[52] U.S. Cl. ............... 205/441; 205/413; 560/18; 560/103
[58] Field of Search ............... 205/413, 441; 560/18, 103

[56] References Cited

U.S. PATENT DOCUMENTS

| | | | |
|---|---|---|---|
| 4,692,545 | 9/1987 | Carter | 560/18 |
| 4,704,467 | 11/1987 | Wehrenberg | 560/18 |
| 5,030,671 | 7/1991 | Wehner et al. | 560/18 |
| 5,366,957 | 11/1994 | Cain et al. | 504/271 |
| 5,424,276 | 6/1995 | Cain et al. | 504/252 |

FOREIGN PATENT DOCUMENTS

| | | |
|---|---|---|
| 2048705 | 2/1992 | Canada. |
| 2075348 | 2/1993 | Canada. |
| 0470856 | 2/1992 | European Pat. Off.. |
| 0524018 | 1/1993 | European Pat. Off.. |
| 0527036 | 2/1993 | European Pat. Off.. |

Primary Examiner—Kathryn L. Gorgos
Assistant Examiner—Edna Wong
Attorney, Agent, or Firm—Connolly and Hutz

[57] ABSTRACT

The invention relates to 2-alkylmercapto-4-(trifluoromethyl)benzoic esters of the formula (II), in which $R^1$ and $R^2$ are, independently of each other, $(C_1-C_6)$ alkyl, and a process for their preparation, which comprises reacting 3,4-dichlorobenzotrifluoride electrochemically at an anode with $CO_2$ to give 2-chloro-4-(trifluoromethyl)-benzoate, converting it into the corresponding benzoic ester of the formula (I), and then reacting it with an alkylmercaptide $R^2S^e$.

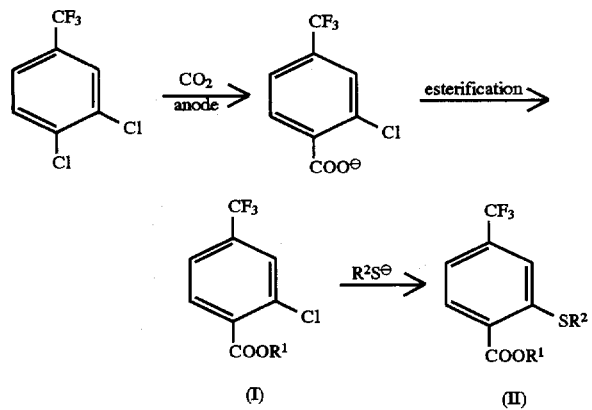

20 Claims, No Drawings

2-ALKYLMERCAPTO-4-(TRIFLUOROMETHYL)BENZOIC ESTERS AND A PROCESS FOR THEIR PREPARATION

The present invention relates to novel 2-alkylmercapto-4-(trifluoromethyl)-benzoic esters and a process for their preparation.

2-Alkylmercapto-4-(trifluoromethyl)benzoic esters are useful intermediates for the preparation of a herbicide which is used in corn (maize) crops (cf. EP 527036, EP 470 856).

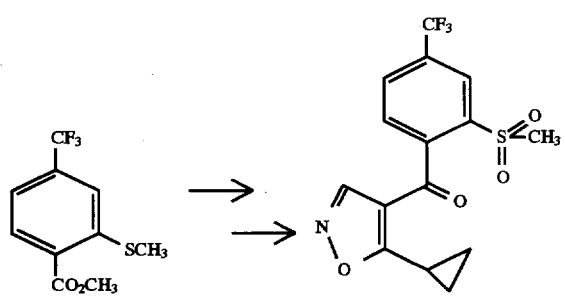

EP 524 018 (Reference Examples 17 and 18) and EP 527 036 (Reference Example 6) describe the preparation of 2-methylmercapto-4-(trifluoromethyl)benzoic acid by the following route:

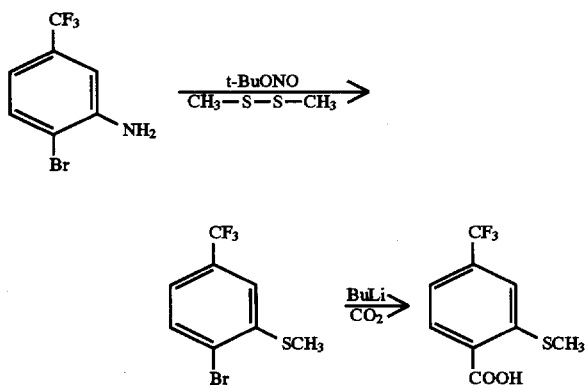

Disadvantages of this method are the starting material, which is difficult to obtain, and the use of organometallic reagents, which lead to safety problems when scaling up the process.

There therefore existed a need for a process which avoids the disadvantages described, which uses easily obtainable starting materials and which is simple to carry out on a large scale, too.

This object is achieved by a process for preparing 2-alkylmercapto-4-(trifluoromethyl)benzoic esters of the formula (II), where $R^1$ and $R^2$ are, independently of each other, ($C_1$–$C_6$) alkyl, which comprises reacting 3,4-dichlorobenzotrifluoride electrochemically at an anode with $CO_2$ to give 2-chloro-4-(trifluoromethyl)benzoate, converting it into the corresponding benzoic ester of the formula (I), and then reacting it with an alkylmercaptide $R^2S^\ominus$.

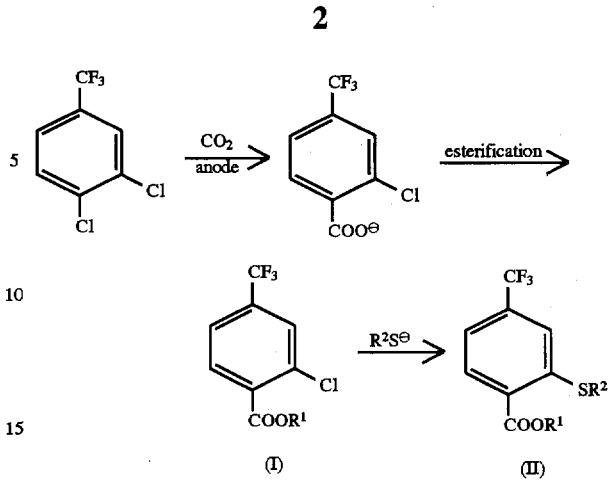

The first step of the synthesis of 2-alkylmercapto-4-(trifluoromethyl)-benzoic esters is the electrochemical reductive carboxylation of 3,4-dichlorobenzotrifluoride to give magnesium 2-chloro-4-(trifluormethyl)benzoate.

The electrochemical apparatus advantageously used for this purpose is an undivided electrolytic cell, which may be of any form, for example a trough-shaped cell or a flow cell, having at least one cathode and one anode. The cathode is made of one of the customary metals, for example aluminum, magnesium, iron, nickel, chromium, titanium, copper, lead, zinc, tin, cadmium, silver, gold, or platinum, or alloys of these metals, or carbon materials, for example graphite or vitreous carbon. Preference is given to using lead, cadmium and tin. The anode is made of metals which are difficult to deposit cathodically under the conditions of electrolysis used, for example aluminum, calcium or, preferably, magnesium.

Suitable electrolytes are aprotic, dipolar solvents, for example acetonitrile, dimethylacetamide, N-methylpyrrolidone, tetrahydrofuran or, preferably, dimethylformamide. Suitable conducting salts are inert salts soluble in the electrolyte, preferably tetraalkylammonium salts. During electrolysis, the electrolyte is saturated with $CO_2$. This can be ensured by a continuous flow of a $CO_2$ stream, or by working in a pressurized cell.

The electrolysis is carried out at temperatures between about 0° C. and 80° C., preferably between 0° C. and 20° C. The electrolysis is carried out at current densities between about 1 and 100 mA/cm², preferably between 5 and 50 mA/cm². During electrolysis, the electrolyte is advantageously moved relative to the electrodes by stirring or streaming.

The second step of the preparation process is the esterification of the electrochemically prepared 2-chloro-4-(trifluoromethyl)benzoate to give 2-chloro-4-(trifluoromethyl)benzoic esters.

The esterification is preferably carried out without prior purification of the crude electrolyte in such a manner that the concentrated crude electrolyte is admixed with the alcohol to be esterified and a strong acid and refluxed. Alternatively, the esterification can be carried out in a 2 phase system, consisting of water and an organic solvent not miscible with water, by using strong alkylating agents, for example dialkyl sulfates. The phase transfer catalysts used here are tetralkylammonium salts, for example tetrabutylammonium hydrogensulfate. The pH is kept at 7 by addition of base or the use of buffer systems.

Products of the formula (I) are, for example, methyl 2-chloro-4-(trifluoromethyl)benzoate, ethyl 2-chloro-4-(trifluoromethyl)benzoate, propyl 2-chloro-4-

(trifluoromethyl)benzoate, isopropyl 2-butyl-2-chloro-4-(trifluoronmethyl)benzoate, 1-butyl-2-chloro-4-(trifluoromethyl)benzoate, 2-butyl-2-chloro-4 (trifluoromethyl)benzoate, isobutyl 2-chloro-4-(trifluoromethyl)benzoate, t-butyl 2-butyl-2-chloro-4-(trifluoromethyl)benzoate, amyl 2-chloro-4-(trifluoromethyl)benzoate, isoamyl 2-chloro-4-(trifluoromethyl)benzoate.

The preparation according to the invention of the 2-alkylmercapto-4-(trifluoromethyl)benzoic esters is carried out by reacting one of the abovementioned 2-chloro-4-(trifluoromethyl)benzoic esters with an alkali metal, alkaline earth metal, or ammonium alkylmercaptide in an organic solvent of the group of the alcohols, ethers, hydrocarbons or aromatic compounds, or another, dipolar solvent such as DMF. The alkylmercaptide can also be prepared in situ by using the alkyl mercaptan in the presence of an inorganic or organic base such as sodium carbonate or a tert-amine.

The reaction with the alkylmercaptide is carried out at temperatures from 0° C. to 150° C. The isolation of the products is carried out for example by evaporation of the solvent and purification of the crude product obtained as a residue by fractional distillation or crystallization.

The invention further relates to compounds of the formula (I), where $R^1$ is ($C_1$–$C_6$) alkyl, and compounds of the formula (II), where $R^1$ and $R^2$ are ($C_1$–$C_6$) alkyl, in particular to compounds of the formula (II) where $R^1$ is ethyl and $R^2$ is methyl and compounds of the formula (I) where $R^1$ is ethyl.

The following examples serve to illustrate the invention:

EXAMPLE 1

The reductive carboxylation of 3,4-dichlorobenzotrifluoride is carried out electrochemically in an undivided electrolytic cell. The cell consists of a cylindrical glass vessel with a cooling mantle and a ground glass lid containing 3 small, ground openings. The anode used is a magnesium plate (length: 110 mm; width: 55 mm; immersion depth: 100 mm), the cathode is a cadmium plate with the same dimensions. The electrodes are fastened to the lid of the cell by stiff wires made from platinum wire, which also carry the electrical current. In addition, the cell is equipped with a gas inlet tube for carbon dioxide combined with a bubble counter. The electrolyte is stirred with a magnetic bar.

The dry cell is initially charged with 350 ml of DMF, 21.5 g of 3,4-dichlorobenzotrifluoride and 2.7 g of tetrabutylammonium bromide. With stirring, a constant stream of $CO_2$ is passed through the electrolyte, to ensure that the solution is saturated with $CO_2$, and after ½ hour the electrolysis is started while stirring and the passing through of a slow stream of $CO_2$ is continued. The amperage is a constant 1.1 A, the temperature 15° C. The voltage of the cell is initially in the range of 3 to 9 V and increases to about 25 V toward the end. The charge quantity is 2 F/mol.

To esterify the benzoic acid formed, the electrolyte is concentrated to dryness at 60° C./15 mbar using a rotary evaporator, the residue obtained is admixed with 250 ml of ethanol and 50 ml of concentrated $H_2SO_4$ and heated for 8 h under reflux. The reaction mixture is poured into 1.8 l of ice-water and extracted with 200 ml of diethyl ether. The ether phase is dried, filtered and concentrated. After distillation of the residue, 11.9 g of ethyl 2-chloro-4-(trifluoromethyl)benzoate are obtained. m.p.: 68° C./6-10$^{-4}$ bar $^1$H-NMR (300 MHz/CDCl$_3$):δ=1.42 (triplet, J=7Hz, CH$_3$) 4.44 (quartet, J=7Hz, CO$_2$CH$_3$) 7.56 (doublet, J=8Hz, 1H$_{arom}$) 7.71 (singlet, 1H$_{arom}$) 7.91 (doublet, J=8Hz, 1H$_{arom}$) ppm

EXAMPLE 2

Example 1 is repeated with n-butanol instead of ethanol, affording butyl 2-chloro-4-(trifluoromethyl)benzoate. m.p.: 90° C./2·10$^{-4}$ bar $^1$H-NMR (300 MHz/CDCl$_3$):δ=0.98 (triplet, J=6Hz, CH$_3$); 1.49 (quartet of triplets, J=6; 8 Hz, CH$_2$); 1.77 (triplet of triplets, J=6; 8 Hz, CH$_2$); 4.39 (triplet, J=6 Hz; CO$_2$CH$_2$); 7.56 (doublet, J=8 Hz, 1Harom); 7.70 (singlet, 1H$_{arom}$); 7.92 (doublet, J=8 Hz, 1H$_{arom}$) ppm.

EXAMPLE 3

A solution of 23.9 g (0.1 mol) of methyl 2-chloro-4-(trifluoromethyl)benzoate and 7.7 g (0.11 mol) of sodium thiomethoxide in 100 ml of DMF is stirred at 50° C. for 6 h. For workup, the reaction mixture is poured onto 400 ml of ice-water and extracted with 150 ml of toluene. The organic phase is separated off, dried over Na$_2$SO$_4$, filtered, and concentrated. After distillation of the residue, 18.7 g of methyl 2-methylmercapto-4-(trifluoromethyl)benzoate are obtained.

b.p.: 90° C./2·10$^{-4}$ bar m.p.: 49°–50° C. $^1$H-NMR (300 MHz/CDCl$_3$): d=2.50 (singlet, SCH$_3$), 3.95 (singlet, CO$_2$CH$_3$), 7.38 (doublet, J=8 Hz, 1H$_{arom}$), 7.47 (singlet, 1H$_{arom}$), 8.08 (doublet, J=8 Hz, 1H$_{arom}$), ppm. MS: m/e=250

EXAMPLE 4

Example 3 is repeated except that 2.53 g (10 mmol) of ethyl 2-chloro-4-(trifluoromethyl)benzoate are reacted with 0.77 g (11 mmol) of sodium thiomethoxide in 15 ml of DMF. 2.5 g of ethyl 2-methylmercapto-4-(trifluoromethyl) benzoate of high purity are obtained. It is therefore not necessary to purify by distillation.

m.p.: 44°–45° C. $^1$H-NMR (300 MHz/CDCl$_3$): d=1.42 (triplet, CH$_3$), 2.50 (singlet, SCH$_3$), 4.42 (quartet, CO$_2$CH$_2$), 7.39 (doublet, J=8 Hz, 1H$_{arom}$), 7.48 (singlet, 1H$_{arom}$), 8.09 (doublet, J=8 Hz, 1H$_{arom}$) ppm. MS: m/e=264

EXAMPLE 5

Example 3 is repeated except that 12.7 g (5 mmol) of ethyl 2-chloro-4-(trifluoromethyl)benzoate are converted into 11.5 g of ethyl 2-propylmercapto-4-(trifluoromethyl) benzoate. n$^{22}_D$=1.5052

$^1$H-NMR (300 MHz/CDCl$_3$):δ=1.10 (triplet, J=7 Hz, CH$_3$); 1.41 (triplet, J=7 Hz, CH$_3$); 1.78 (quartet of triplets, J=7; 7 Hz, CH$_2$); 2.93 (triplet, J=7 Hz, SCH$_2$); 4.42 (quartet, J=7 Hz, CO$_2$CH$_2$); 7.34 (doublet, J=8 Hz, 1 H$_{arom}$); 7.52 (singlet, 1H$_{arom}$); 8.02 (doublet, J=8 Hz, 1H$_{arom}$) ppm.

EXAMPLE 6

Example 3 is repeated except that 12.6 g of butyl 2-chloro-4-(trifluoromethyl)benzoate (45 mmol) are converted into 11 g of butyl 2-propylmercapto-4-(trifluoromethyl)benzoate. n$^{22}_D$=1.4996

$^1$H-NMR (300 MHz/CDCl$_3$):δ=0.98 (triplet, J=7 Hz, CH$_3$); 1.10 (triplet, J=7 Hz, CH$_3$); 1.49 (quartet of triplets, J=8; 7 Hz, CH$_2$); 1.78 (multiplet, 2×CH$_2$); 2.94 (triplet, J=7 Hz, SCH$_2$); 4.36 (triplet, J=7 Hz, CO$_2$CH$_2$); 7.36 (doublet, J=8 Hz, 1H$_{arom}$); 7.52 (singlet, 1H$_{arom}$); 8.03 (doublet, J=8 Hz, 1H$_{arom}$) ppm.

What is claimed is:

1. A process for preparing 2-alkylmercapto-4-(trifluoromethyl)benzoic esters of the formula (II), where $R^1$ and $R^2$ are, independently of each other, $C_1$–$C_6$ alkyl, which comprises reacting 3,4-dichlorobenzotrifluoride electrochemically at an anode with $CO_2$ to give 2-chloro-4-

(trifluoromethyl)benzoate, converting the 2-chloro-4-(trifluoromethyl)benzoate into a corresponding benzoic ester of the formula (I), and then reacting the corresponding benzoic ester of the formula (I) with an alkylmercaptide $R^2S^\ominus$:

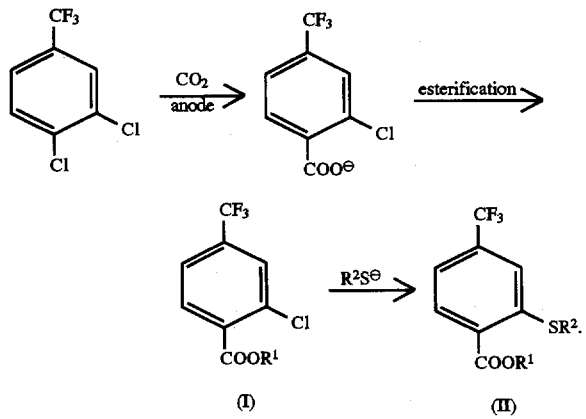

2. A process as claimed in claim 1, wherein the reaction of 3,4-dichlorobenzotrifluoride is carried out in an undivided electrolytic cell having a cathode, where the cathode is made of aluminum, magnesium, iron, nickel, chromium, titanium, copper, lead, zinc, tin, cadmium, silver, gold, platinum, alloys of these metals, or carbon materials, and the anode is made of aluminum, calcium, or magnesium.

3. A process as claimed in claim 2, wherein the cathode is made of lead, cadmium, or tin, and the anode is made of magnesium.

4. A process as claimed in claim 1, wherein an electrolyte is used during said reaction and the electrolyte is a dipolar aprotic solvent.

5. The process as claimed in claim 4, wherein said dipolar aprotic solvent is acetonitrile, dimethylacetamide, N-methylpyrrolidone, tetrahydrofuran or dimethylformamide and the reaction is carried out at a temperature of 0° to 20° C. and a current density of 5 to 50 mA/cm².

6. The process as claimed in claim 5, wherein said dipolar aprotic solvent is dimethylformamide and esterification is carried out in a 2 phase system with dialkyl sulfates.

7. The process as claimed in claim 6, wherein the 2-chloro-4-(trifluoromethyl)benzoate is converted into the benzoic ester of the formula I by esterification and said esterification is carried out by reacting a concentrated crude electrolyte with an alcohol $R^1OH$ and HCl or $H_2SO_4$.

8. The process as claimed in claim 6, wherein $R^1$ is ethyl and $R^2$ is methyl.

9. A process as claimed in claim 4, wherein the electrolyte is saturated with $CO_2$ during electrolysis.

10. A process as claimed in claim 1, wherein the reaction is carried out at temperatures of 0° to 80° C. and at current densities of 1 to 100 mA/cm².

11. A process as claimed in claim 1, wherein the 2-chloro-4-(trifluoromethyl)benzoate is converted into the benzoic ester of the formula I by esterification and said esterification is carried out by reacting a concentrated crude electrolyte with an alcohol $R^1OH$ and a strong acid.

12. A process as claimed in claim 1, wherein the 2-chloro-4-(trifluoromethyl)benzoate is converted into the benzoic ester of the formula I by esterification and said esterification is carried out in a 2 phase system with strong alkylation agents under phase transfer catalysts.

13. A process as claimed in claim 1, wherein the alkylmercaptide is an alkali metal mercaptide, an alkaline earth metal mercaptide or an ammonium mercaptide.

14. A process as claimed in claim 1 wherein the alkylmercaptide is formed in situ from an alkyl mercaptan and a base.

15. A process as claimed in claim 1, wherein $R^2$ is methyl.

16. A process as claimed in claim 1, wherein $R^1$ is methyl or ethyl.

17. A compound of the formula (II)

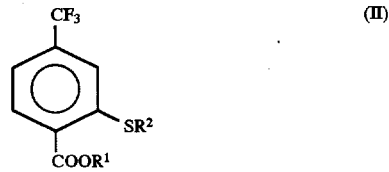

in which $R^1$ and $R^2$ are identical or different and are $C_1$–$C_8$ alkyl.

18. The compound as claimed in claim 17, wherein $R^1$ is ethyl and $R^2$ is methyl.

19. A compound of the formula (I)

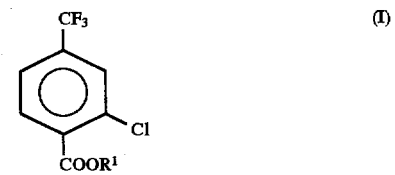

in which $R^1$ is $C_1$–$C_6$-alkyl.

20. The compound as claimed in claim 19, wherein $R^1$ is ethyl.

* * * * *